United States Patent
Huboux

(10) Patent No.: US 7,157,417 B2
(45) Date of Patent: Jan. 2, 2007

(54) HINDERED KETONES AS PERFUMING INGREDIENTS

(75) Inventor: Alexandre Huboux, Pringy (FR)

(73) Assignee: Firmenich SA, Geneva (CH)

( * ) Notice: Subject to any disclaimer, the term of this patent is extended or adjusted under 35 U.S.C. 154(b) by 24 days.

(21) Appl. No.: 10/952,462

(22) Filed: Sep. 28, 2004

(65) Prior Publication Data

US 2005/0043211 A1 Feb. 24, 2005

Related U.S. Application Data

(63) Continuation of application No. PCT/IB03/01813, filed on May 1, 2003.

(30) Foreign Application Priority Data

May 29, 2002 (WO) .................. PCT/IB02/01961

(51) Int. Cl.
*A61Q 13/00* (2006.01)
(52) U.S. Cl. .................. 512/26; 568/303; 568/376; 568/377
(58) Field of Classification Search ................ 512/26; 568/303, 376, 377
See application file for complete search history.

(56) References Cited

U.S. PATENT DOCUMENTS

| | | | |
|---|---|---|---|
| 3,923,898 A | 12/1975 | Schulte-Elte | 260/586 P |
| 4,136,119 A * | 1/1979 | Hunter et al. | 568/338 |
| 4,173,584 A | 11/1979 | Dastur | 260/586 R |

OTHER PUBLICATIONS

Takenori Kusumi et al., "Acid-Catalyzed Cyclization of 2,3-Dimethyl-2-phenethyl-3-cyclohexen-1-One", Department of Chemistry, Tokyo Kyoiku University, Otsuka, Bunkyo-ku, Tokyo 112, Bulletin Of The Chemical Society Of Japan, vol. 48, No. 1 pp. 96-100 (1975).
Jean-Marie Conia, XP002247100, "Alcoylation des cétones par l'intermédiaire de l'amylate tertiaire de sodium. ( 4$^e$ Memoire). Cétones éthyléniques:IIe partie: Alcoylation en série alicyclique", Bulletin De La Societe Chimique De France., pp. 943-948, Societe Francaise Ide Chimie. Paris., FR (1954).
Metge, Claude et al., XP 002247099, "Determination de la configuration et de la conformation de dérivés alcoylés de la (-)-methone" Bulletin De La Societe Chimique De France., (3) (PT. 2) pp. 1049-1053, (1973).

* cited by examiner

*Primary Examiner*—Monique T. Cole
(74) *Attorney, Agent, or Firm*—Winston & Strawn LLP

(57) ABSTRACT

The present invention relates to the perfumery industry. It concerns more particularly a β-γ unsaturated hindered ketone of formula

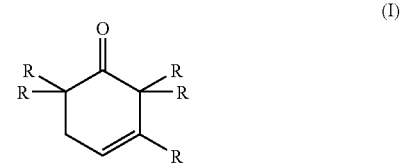

(I)

wherein R represents, simultaneously or independently, a $C_1$ to $C_4$ linear or branched alkyl group, and in the form of any one of its isomers, i.e. optical isomers or diastereoisomers, or of a mixture thereof. The use of the compound as a perfuming ingredient, as well as the perfumed articles or perfuming compositions that contain as an active ingredient a compound of formula (I), are also embodiments of the invention.

11 Claims, No Drawings

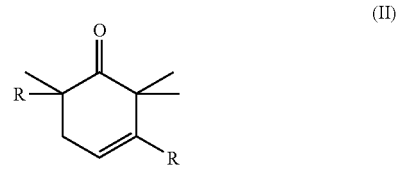

HINDERED KETONES AS PERFUMING INGREDIENTS

CROSS-REFERENCE TO RELATED APPLICATIONS

This application is a continuation of International application no. PCT/IB03/01813 filed May 1, 2003, the entire content of which is expressly incorporated herein by reference thereto.

TECHNICAL FIELD

The present invention relates to the perfumery industry. It concerns more particularly a hindered β-γ unsaturated ketone of formula

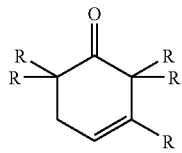

(I)

wherein R represents a $C_1$ to $C_4$ linear or branched alkyl group. The invention also relates to the use of the invention compounds as perfuming ingredients as well as to the perfumed articles or perfuming compositions comprising as active ingredient a compound of formula (I).

BACKGROUND

To the best of our knowledge, none of the compounds of formula (I) has been reported in the literature. The prior art reports only a compound which has an analogue structure when compared with the ketone of the invention. T. Kusumi et al. in Bull. Chem. Soc. Jpn.; 1975, 48, 96, disclose the synthesis, as well as the use as chemical intermediate, of 2-phenethyl-2,3,6,6-tetramethyl-cyclohex-3-enone. However, the authors, in their report, are mute regarding any olfactive properties of the compound mentioned above.

SUMMARY OF THE INVENTION

Surprisingly, we have now been able to establish that a compound of formula

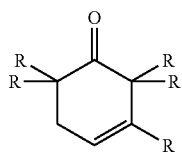

(I)

wherein R represents, simultaneously or independently, a $C_1$ to $C_4$ linear or branched alkyl group, and in the form of any one of its isomers, i.e. optical isomers or diastereoisomers, or of a mixture thereof;

possesses useful perfuming properties, of the woody and/or aromatic type, which render it a very useful ingredient for the perfume industry.

DETAILED DESCRIPTION OF THE PREFERRED EMBODIMENTS

A compound of formula (II)

wherein R represents, simultaneously or independently, a $C_1$ to $C_3$ linear or branched alkyl group, and in the form of any one of its isomers, i.e. optical isomers or diastereoisomers, or of a mixture thereof, represents a preferred embodiment of the invention.

By means of example of the compounds of formula (II), one can cite 3-isopropyl-2,2,6,6-tetramethyl-3-cyclohexen-1-one which is much appreciated by perfumers for its warm and rich fragrance. Said fragrance is characterized by a very pleasant and remarkable woody odor having a vetyverol and a more pronounced agarwood connotation. Moreover, the fragrance of the said compound possesses also amber and camphoraceous notes as well as a fruity, e.g. grapefruit, and a slightly aromatic-thuyonic note. The above mentioned compound is thus able to impart to a perfuming composition an interesting, and quite unusual, warm and rich woody-amber-agarwood connotation which is often superior to the one imparted by other known perfuming ingredients of the same olfactory family, i.e. woody family, such as Vetyverol, Vetyverone or Kephalis (origin: Givaudan SA, Switzerland).

Another example of a preferred compound of the invention is 6-isopropyl-2,2,3,6-tetramethyl-3-cyclohexen-1-one, which has a camphoraceous, eucalyptus and pine-woody odor together with earthy, aromatic, green and citrus notes.

As mentioned above, the invention also concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of the compound (I) in any of its forms which can be advantageously employed in perfumery as active ingredients.

These forms are also an object of the present invention.

In an embodiment of the invention, one of the forms, which can be advantageously employed as perfuming ingredient, is a composition of matter consisting of at least a compound of formula (I) and at least one perfumery carrier.

By "perfumery carrier" we mean here one or more materials which are able to be admixed with an invention's compound without significantly altering its organoleptic properties, e.g. materials which are practically neutral from a perfumery point of view. Said carrier may be a liquid or a solid. As liquid carrier one may cite, as non-limiting examples, an emulsifying system, i.e. a solvent and a surfactant system, or a solvent commonly used in perfumery. As examples of solvents commonly used in perfumery, generally speaking, one can cite compounds such as dipropyleneglycol, diethyl phthalate, isopropyl myristate, benzyl benzoate, 2-(2-ethoxyethoxy)-1-ethanol or ethyl citrate, which are the most commonly used. Non-limiting examples of solid carrier are absorbing gums or polymers, or yet encapsulating materials, such as wall-forming and plasticizing materials.

In another embodiment of the invention, a suitable form of the invention's compounds is a composition of matter comprising at least one compound of formula (I) and a perfume base. In other words the compound (I) is in the form of a perfuming composition. It is understood that the perfuming ingredients are present in a perfuming effective amount.

Generally speaking, by "perfume base" we mean here a composition comprising at least one perfuming co-ingredient and possibly one or more solvents or adjuvants commonly used in the perfume industry.

These perfuming co-ingredients are not of the formula (I) and may be in any of their forms. Moreover, by "perfuming co-ingredient" it is also meant here a compound, which is of current use in perfumery industry, i.e. a compound which is used as ingredient in perfuming preparation or composition in order to impart an hedonic effect. In other words such a co-ingredient, to be considered as being a perfuming one, must be recognized by a person skilled in the art as being able to impart or modify in a positive or pleasant way the odor of a composition, and not just as having an odor. Its is therefore understood here that, unless otherwise indicated or described, any mixture resulting directly from a chemical synthesis in which the compound of the invention is involved as a starting intermediate or as an end-product is not a perfuming composition according to the invention.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

Similarly, a detailed description of the nature and type of solvents commonly used in perfuming bases cannot be exhaustive. A skilled person in the art is able to select them on the basis of the nature of the product to be perfumed. However, as non-limiting examples of solvents commonly used in perfumery bases, one can cite, in addition to the solvents mentioned above, also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

The perfuming compositions according to the invention may be a simple mixture of the various co-ingredients and solvents, or be also in the form of an emulsion or microemulsion. Alternatively, said perfuming compositions can be incorporated into a solid perfumery carrier, as defined above.

It is useful to mention here that the possibility of having, in the compositions of matter mentioned above, more than one compound of formula (I) is important as it enables the perfumer to prepare accords or perfumes, possessing the odor tonality of various compounds of the invention, creating thus new tools for their work.

Furthermore, as mentioned above, a compound of formula (I) is a useful perfuming ingredient and therefore can be advantageously used in all the fields of modern perfumery to positively impart or modify the odor of a consumer product into which said compound (I), in any of its form, is added. Consequently, a perfumed article comprising:

i) at least one compound of formula (I), or any of the compositions of matter mentioned above; and
ii) a consumer product base, is also an object of the present invention.

For the sake of clarity, it has to be mentioned that, by "consumer product base" we mean here an unperfumed consumer product, i.e. a consumable product such as a detergent or a perfume, or a part of said consumer product. In other words, a perfumed article according to the invention comprises at least a part of the whole formulation corresponding to a desired consumer product, e.g. a detergent, and an olfactive effective amount of at least an invention's compound, in any of its forms.

The nature and type of the constituents of the consumer product do not warrant a more detailed description here, which in any case would not be exhaustive, the skilled person being able to select them on the basis of its general knowledge and according to the nature and the desired effect of said product.

Suitable unperfumed consumer products comprise solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compounds, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, concentrations from 0.1% to 30%, and preferably from 1% to 5%, by weight of these compounds, with respect to the perfuming composition in which they are incorporated, can be typically used. Concentrations lower than these can be used when these compounds are incorporated into perfumed articles.

EXAMPLES

The invention will now be described in further details by way of the following examples, wherein the temperatures are indicated in degrees centigrade (° C.); $^1$H-NMR spectral data were recorded at 360 MHz and $^{13}$C NMR spectra were recorded at 90 MHz in CDCl$_3$, the chemical displacements δ are indicated in ppm with respect to the TMS as standard, the coupling constant J are expressed in Hz and all the abbreviations have the usual meaning in the art.

Example 1

Synthesis of 3-isopropyl-2,2,6,6-tetramethyl-3-cyclohexen-1-one

Potassium hydride (13.2 g of a 35% suspension in mineral oil, 115 mmol) was washed with pentane and suspended in 45 ml of THF. To said suspension was added over 5 minutes 3-isopropyl-6-methyl-3-cyclohexen-1-one (92% purity, obtained according to G. Dupont et al. in Bull. Chem. Soc. France, 1955, 621) (3.33 g, 21.9 mmoles) dissolved in 5 ml of THF. The resulting suspension was stirred at room temperature for 30 minutes and afterwards, while cooling the reaction medium with an ice bath so that the temperature was kept below 15° C., methyl iodide (6.8 ml, 109 mmol) was added over 25 minutes. The reaction mixture was stirred 30 minutes at room temperature and then hydrolysed with aqueous (15%) sodium hydroxide. The aqueous phase was extracted with ether and the combined organic phases washed twice with water, dried over magnesium sulphate and concentrated to give 5.28 g of a yellow oil. The latter was purified by chromatography over silica gel (elution with 0–2% ethyl acetate/heptane) and a subsequent preparative gas chromatography followed by concentration of the appropriate fractions. It was thus obtained 3.05 g (yield=78%) of the title product.

$^1$H-NMR: 5.59(t, J=4.7 Hz, 1H), 2.32(sept, J=7.0 Hz, 1H), 2.17(d, J=4.7 Hz, 2H), 1.17(s, 6H), 1.11(s, 6H), 1.10(d, J=7.0 Hz, 6H). $^{13}$C-NMR: 219.8, 150.8, 116.1, 47.7, 42.8, 37.7, 28.2, three C at 25.4, two C at 24.9, 24.7.

Example 2

Synthesis of 6-isopropyl-2,2,3,6-tetramethyl-3-cyclohexen-1-one

Potassium hydride (10.5 g of a 35% suspension in mineral oil, 92 mmol) was washed with pentane and suspended in 25 ml of THF. To said suspension was added over 5 minutes p-menth-6-en-3-one (90% purity, obtained according to G. Dupont et al. in Bull. Chem. Soc. France, 1955, 621) (2.80 g, 18.4 mmoles) dissolved in 5 ml of THF. The resulting suspension was stirred at room temperature for 30 minutes and afterwards, while cooling the reaction medium with an ice bath so that the temperature was kept below 20° C., methyl iodide (5.8 ml, 92 mmol) was added over 30 minutes. The reaction mixture was stirred 10 minutes at room temperature and then hydrolysed with aqueous (15%) sodium hydroxide and water. The aqueous phase was extracted with ether and the combined organic phases washed with brine, dried over magnesium sulphate and concentrated to give 3.61 g of a yellow oil. The latter was purified by chromatography over silica gel (elution with 2% ethyl acetate/heptane) and a subsequent preparative gas chromatography followed by concentration of the appropriate fractions. It was thus obtained 2.1 g (yield=66%) of the title product.

$^1$H-NMR: 5.51(m, 1H), 2.29(ddq, J=17, 5.1, 1.6 Hz, 1H), 2.20(sept, J=6.7 Hz, 1H), 1.95(ddq, J=17, 4.3, 2.0 Hz, 1H), 1.73(dd, J=3.2, 1.6 Hz, 3H), 1.17(s, 3H), 1.11(s, 3H), 0.94(s, 3H), 0.81(d, J=6.7 Hz, 3H), 0.77(d, J=7.1 Hz, 3H). $^{13}$C-NMR: 219.3, 139.8, 118.7, 49.1, 47.2, 31.1, 29.9, 24.8, 24.7, 19.6, 18.7, 17.3, 17.1.

Example 3

Preparation of a Perfuming Composition

A woman perfume base composition of the "floral, woody and musky" type was prepared by admixing the following ingredients:

| Ingredient | Parts by weight |
|---|---|
| Styrallyl acetate | 5 |
| 10%* Aldehyde C 10 | 10 |
| 10%* Undecylenic aldehyde | 10 |
| Ambrox ®[1] | 30 |
| Bacdanol ®[2] | 20 |
| Cedroxyde ®[3] | 40 |
| Coumarine | 10 |
| 10%* Incense essential oil | 50 |
| Exaltolide ®[4] | 100 |
| 10%* Farenal[5] | 5 |
| 10%* Pine needle essential oil | 25 |
| (1'R,2R)-2-methyl-4-(2',2',3'-trimethyl-3'-cyclopenten-1'-yl)-4-penten-1-ol | 10 |
| 10%* Galbanum essential oil | 25 |
| Geranium essential oil | 5 |
| Clove essential oil | 5 |
| Habanolide ®[6] | 150 |
| Hedione ® HC[7] | 150 |
| Helvetolide ®[8] | 50 |
| beta-Ionone | 5 |
| Iralia ®[9] | 80 |
| Iso E Super[10] | 120 |
| 10%* Labdanum essential oil | 20 |
| Lilial ®[11] | 100 |
| Lyral | 70 |
| 1,2-Dimethoxy-4-(1-propenyl)benzene | 10 |
| Cristal moss | 10 |
| 10%* Oak moss essential oil | 30 |
| Muscenone Delta[12] | 50 |
| 10%* Rose oxyde | 10 |
| Sclary sage essential oil | 10 |
| gamma-Undecalactone | 10 |
| Bergamote essential oil | 60 |
| 10%* Castoreum[13] | 15 |
| Californian lemon essential oil | 70 |
| 10%* Civette | 20 |
| Orange flowers essential oil | 10 |
| Jasmin essential oil | 30 |
| Muguet[13] | 50 |
| Neroli Bigarde[13] | 10 |
| Tamarine Base 41310 G[13] | 20 |
| Vanille essential oil | 30 |
| Wardia ®[13] | 20 |
| Ylang I | 40 |
| Total | 1600 |

*in dipropyleneglycol
[1] dodecahydro-3a,6,6,9a-tetramethyl-nathptho[2,1-b]furan; origin: Firmenich SA, Geneva, Switzerland
[2] 2-ethyl-4-(2,2,3-trimethyl-3-cyclopenten-1-yl)-2-buten-1-ol; origin: IFF, USA
[3] (E,E)-9,10-epoxy-1,5,9-trimethyl-1,5-cyclododecadiene; origin: Firmenich SA, Geneva, Switzerland
[4] oxacyclohexadecan-2-one; origin: Firmenich SA, Geneva, Switzerland
[5] origin: Haarmann & Reimer
[6] pentadecenolide; origin: Firmenich SA, Geneva, Switzerland
[7] methyl dihydrojasmonate; origin: Firmenich SA, Geneva, Switzerland
[8] (+)-(1S,1'R)-2-[1-(3',3'-dimethyl-1'-cyclohexyl)ethoxy]-2-methylpropyl propanoate; origin: Firmenich SA, Geneva, Switzerland
[9] methyl ionone; origin: Firmenich SA, Geneva, Switzerland
[10] origin: IFF, USA
[11] origin: Givaudan SA, Vernier, Switzerland
[12] 3-methyl-(4 and 5)-cyclopentadecen-1-one; origin: Firmenich SA, Geneva, Switzerland
[13] compounded perfumery base; origin: Firmenich SA, Geneva, Switzerland The addition of 50 parts by weight of 3-isopropyl-2,2,6,6-tetramethyl-3-cyclohexen-1-one imparts to the above-mentioned floral accord a good woody connotation reminiscent of the Vetyver roots odor, and having also the watery note of Vetyverol. The overall olfactive effect provided by 3-isopropyl-2,2,6,6-tetramethyl-3-cyclohexen-1-one was by far superior to the one which could have been obtained by the addition of an equivalent amount of Kephalis (origin: Givaudan SA, Switzerland).

Example 4

Preparation of a Perfuming Composition

An "aromatic, aldehyde and spicy" type Eau de toilette for man was prepared by admixing the following ingredients:

| Ingredient | Parts by weight |
|---|---|
| 10%* Aldehyde MNA | 100 |
| Ambrox ®[1] | 50 |
| 50%* Anthralal | 25 |
| L-Carvone | 25 |
| Citral | 10 |
| Californian lemon essential oil | 50 |
| Coumarine | 20 |
| Dihydromyrcenol | 200 |
| Eugenol | 100 |
| Bacdanol ®[2] | 50 |
| Habanolide ®[3] | 410 |
| Hedione ® HC[4] | 200 |
| Iralia ®[5] Total | 50 |
| 10%* Isobutylquinoleine | 50 |
| Lavandin essential oil | 50 |
| Lilial ®[6] | 200 |
| Linalol | 100 |
| 1,2-Dimethoxy-4-(1-propenyl)benzene | 25 |
| Nutmeg essential oil | 50 |
| Olibanum essential oil | 30 |
| 10%* Methyl phenylacetate | 10 |
| Sclary sage essential oil | 50 |
| Red thyme essential oil | 15 |
| 10%* Triplal[7] | 30 |
| 10%* Vanilline | 80 |
| Basilic essential oil | 50 |
| Bergamote essential oil | 220 |
| Ceylan cinnamon essential oil | 50 |
| Galbex 183 ®[8] | 50 |
| Geranium essential oil | 20 |
| Jasmin[8] | 40 |
| Tamarine Base 41310 G[8] | 40 |
| Wardia ®[8] | 20 |
| Ylang I | 30 |
| Total | 2500 |

*in dipropyleneglycol
[1])dodecahydro-3a,6,6,9a-tetramethyl-nathptho[2,1-b]furan; origin: Firmenich SA, Geneva, Switzerland
[2])2-ethyl-4-(2,2,3-trimethyl-3-cyclopenten-1-yl)-2-buten-1-ol; origin: IFF, USA
[3])pentadecenolide; origin: Firmenich SA, Geneva, Switzerland
[4])methyl dihydrojasmonate; origin: Firmenich SA, Geneva, Switzerland
[5])methyl ionone; origin: Firmenich SA, Geneva, Switzerland
[6])origin: Givaudan SA, Vernier, Switzerland
[7])origin: IFF, USA
[8])compounded perfumery base; origin: Firmenich SA, Geneva, Switzerland The addition of 500 parts by weight of 3-isopropyl-2,2,6,6-tetramethyl-3-cyclohexen-1-one imparted to the hereinabove-mentioned composition a very nice and pleasant woody and rooty note which is reminiscent of Agarwood.

Example 5

Preparation of a Perfuming Composition

A "citrus, woody" type cologne for men was prepared by admixing the following ingredients:

| Ingredient | Parts by weight |
|---|---|
| Linalyl acetate | 500 |
| Bergamote essential oil | 200 |
| Citral | 20 |
| Sfuma lemon | 100 |
| Civette | 30 |
| Coumarine | 80 |
| Geranium essential oil | 30 |
| Hedione ® HC[1] | 550 |
| linalool | 90 |
| Sfuma mandarine essential oil | 70 |
| 50%* Oak moss essential oil | 40 |
| Polysantol ®[2] | 50 |
| Lavandin essential oil | 180 |
| Lyral | 300 |
| Patchouli | 720 |
| Vanille essential oil | 40 |
| Total | 3000 |

*in dipropyleneglycol
[1])methyl dihydrojasmonate; origin: Firmenich SA, Geneva, Switzerland
[2])3,3-dimethyl-5-(2',2',3'-trimethyl-3'-cyclopenten-1'-yl)-4-penten-2-ol; origin: Firmenich SA, Geneva, Switzerland The addition of 500 parts by weight of 3-isopropyl-2,2,6,6-tetramethyl-3-cyclohexen-1-one to the hereinabove-mentioned man's cologne enhanced the natural connotation of the latter, which was provided by the patchouli, by bringing a rooty and slightly thuyonic-aromatic dimension.

What is claimed is:

1. A method to confer, enhance, improve or modify the odor properties of a perfuming composition or of a perfumed article, which method comprises adding to said composition or article an effective amount of at least a compound of formula (I)

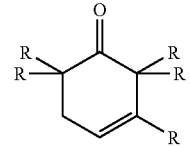

(I)

wherein R represents, simultaneously or independently, a $C_1$ to $C_4$ linear or branched alkyl group, and in the form of any one of its isomers or of a mixture thereof, in order to provide woody or aromatic odor notes to the composition or article.

2. A method according to claim 1, wherein the compound is of formula

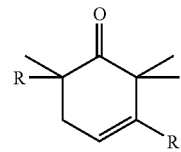

(II)

wherein R represents, simultaneously or independently, a $C_1$ to $C_3$ linear or branched alkyl group, and in the form of any one of its isomers or of a mixture thereof.

3. A method according to claim 2, wherein the compound is 3-isopropyl-2,2,6,6-tetramethyl-3-cyclohexen-1-one or 6-isopropyl-2,2,3,6-tetramethyl-3-cyclohexen-1-one.

4. A method according to claim 1, wherein the composition or article includes at least one perfumery carrier or perfume base.

5. A method according to claim 1, wherein the composition or article includes a consumer product base.

6. A method according to claim 5, wherein the consumer product base is a solid or liquid detergent, a fabric softener, a perfume, a cologne, an after-shave lotion, a perfumed soap, a shower or bath salt, mousse, oil or gel, a hygiene product, a hair care product, a shampoo, a body-care product, a deodorant, a antiperspirant, an air freshener, a cosmetic preparation, a fabric refresher, an ironing water, a paper, a wipe or a bleach.

7. A method according to claim 2, wherein the composition or article includes a consumer product base.

8. A method according to claim 7, wherein the consumer product base is a solid or liquid detergent, a fabric softener, a perfume, a cologne, an after-shave lotion, a perfumed soap, a shower or bath salt, mousse, oil or gel, a hygiene product, a hair care product, a shampoo, a body-care product, a deodorant, a antiperspirant, an air freshener, a cosmetic preparation, a fabric refresher, an ironing water, a paper, a wipe or a bleach.

9. A method according to claim 3, wherein the composition or article includes a consumer product base.

10. A method according to claim 9, wherein the consumer product base is a solid or liquid detergent, a fabric softener, a perfume, a cologne, an after-shave lotion, a perfumed soap, a shower or bath salt, mousse, oil or gel, a hygiene product, a hair care product, a shampoo, a body-care product, a deodorant, a antiperspirant, an air freshener, a cosmetic preparation, a fabric refresher, an ironing water, a paper, a wipe or a bleach.

11. A method according to claim 10, wherein the consumer product base is a solid or liquid detergent, a fabric softener, a perfume, a cologne, an after-shave lotion, a perfumed soap, a shower or bath salt, mousse, oil or gel, a hygiene product, a hair care product, a shampoo, a body-care product, a deodorant, a antiperspirant, an air freshener, a cosmetic preparation, a fabric refresher, an ironing water, a paper, a wipe or a bleach.

* * * * *